US007393857B2

(12) United States Patent
Mueller et al.

(10) Patent No.: US 7,393,857 B2
(45) Date of Patent: *Jul. 1, 2008

(54) USE OF 5-HT₃ RECEPTOR ANTAGONISTS FOR TREATING MUSCULOSKELETAL DISEASES

(75) Inventors: Wolfgang Mueller, Binningen (CH); Thomas Stratz, Bad Saeckingen (DE); Lothar Faerber, Heroldsberg (DE)

(73) Assignee: Novasearch AG, Zug (CH)

( * ) Notice: Subject to any disclaimer, the term of this patent is extended or adjusted under 35 U.S.C. 154(b) by 154 days.

This patent is subject to a terminal disclaimer.

(21) Appl. No.: 10/224,938

(22) Filed: Aug. 21, 2002

(65) Prior Publication Data

US 2003/0008809 A1    Jan. 9, 2003

Related U.S. Application Data

(60) Division of application No. 09/929,454, filed on Aug. 14, 2001, now Pat. No. 6,462,065, which is a continuation of application No. PCT/EP00/01269, filed on Feb. 16, 2000.

(30) Foreign Application Priority Data

Feb. 18, 1999  (GB)  ................................. 9903761.6
Jun. 25, 1999  (GB)  ................................. 9914949.4
Nov. 25, 1999  (GB)  ................................. 9927877.2

(51) Int. Cl.
*A61K 31/4747* (2006.01)
*A61K 31/4178* (2006.01)

(52) U.S. Cl. ........................ 514/278; 514/397; 514/394; 514/396; 514/299

(58) Field of Classification Search ................ 514/397, 514/299, 394, 396, 214, 216, 412, 413, 278
See application file for complete search history.

(56) References Cited

U.S. PATENT DOCUMENTS

| 4,877,798 | A | * | 10/1989 | Sorensen | 514/317 |
| 5,063,230 | A | | 11/1991 | Pelletier et al. | 514/213 |
| 5,063,231 | A | | 11/1991 | Sanger et al. | 514/214 |
| 5,122,528 | A | | 6/1992 | Imondi | 514/295 |
| 5,202,333 | A | | 4/1993 | Berger et al. | 514/296 |
| 5,225,407 | A | | 7/1993 | Oakley et al. | 514/215 |
| 5,378,686 | A | * | 1/1995 | Bennett | 514/12 |
| 5,442,078 | A | | 8/1995 | Cohen et al. | 549/23 |
| 5,491,148 | A | | 2/1996 | Berger et al. | 546/133 |
| 5,576,317 | A | * | 11/1996 | Gonsalves | 514/231.2 |
| 5,703,240 | A | * | 12/1997 | Armour et al. | 546/210 |
| 5,707,642 | A | * | 1/1998 | Yue | 424/423 |
| 5,710,161 | A | * | 1/1998 | Ladduwahetty et al. | 514/278 |
| 5,800,385 | A | | 9/1998 | Demopulos et al. | 604/49 |
| 5,820,583 | A | | 10/1998 | Demopulos et al. | 604/49 |
| 5,860,950 | A | | 1/1999 | Demopulos et al. | 604/49 |
| 6,009,875 | A | * | 1/2000 | Hubbard, Jr. | 128/898 |
| 6,048,859 | A | * | 4/2000 | Dorn et al. | 514/227.5 |
| 6,211,171 | B1 | * | 4/2001 | Sawynok et al. | 514/211.13 |
| 6,384,042 | B2 | * | 5/2002 | Farber et al. | 514/278 |
| 6,462,065 | B2 | * | 10/2002 | Muller et al. | 514/397 |
| 6,541,523 | B2 | * | 4/2003 | Iglehart, III | 514/654 |
| 6,623,742 | B2 | * | 9/2003 | Voet | 424/236.1 |
| 6,642,240 | B2 | * | 11/2003 | Alvaro et al. | 514/255.03 |

FOREIGN PATENT DOCUMENTS

| DE | 10221831 | * | 2/2004 |
| EP | 0 189 002 | | 7/1986 |
| EP | 0 507 637 A2 | | 10/1992 |
| WO | WO 94/01095 | | 1/1994 |
| WO | WO 95/01793 | | 1/1995 |
| WO | WO 9527490 A1 | * | 10/1995 |
| WO | WO 96/19233 | | 6/1996 |
| WO | WO 9853815 A1 | * | 12/1998 |
| WO | WO 00/48597 | | 8/2000 |

OTHER PUBLICATIONS

"Fibromyalgia", The Merck Manual Online Medical Library, www.meck.com, 2003.*
"Fibromyalgia", Goldenberg, D.L, www.patients.uptodate.com, 2007.*
"Localized fibromyalgia in a child", Bassan et al., Pediatric Anesthesia, abstract, vol. 5(4), pp. 263-265.*
Chemical Abstracts AN 125:317390 "Serotoninergic Antagonists as Topical Antipruritic Agents", (Japan 0082176, Aug. 27, 1996).
Chemical Abstracts XP-002149134 Giordano et al., "Topical Ondansetron Attenuates Nociceptive and Inflammatory Effects of Intradermal Capsaicin in Humans", Europ. J. of Pharmacol., vol. 354, No. 1, pp. R13-R14 (1998).
Chemical Abstracts XP-002149139 Schwörer et al., "Treatment of Acute Gouty Arthritis With the 5-Hydroxytryptamine Antagonist Ondansetron", Clin. Investig., vol. 72, No. 10, pp. 811-813 (1994).
Mansford, "Zeichen Für Einen Großen Aufbruch", Fortschritte der Med., vol. 108, Suppl. 82, pp. 4-9 (1990).
Society for Neuroscience, vol. 23, pp. 1540-1541 (1997)—[Abstracts 601.15-602.8].
Barnes et al., "Modulation of Neurogenic Inflammation: Novel Approaches to Inflammatory Disease", Trends in Pharmacol. Sci. (TiPS), vol. 11, pp. 185-189 (1990).
Giordano et al., "Peripherally Administered Serotonin 5-HT₃ Receptor Antagonists Reduce Inflammatory Pain in Rats", Europ. J. of Pharmacol., vol. 170, Nos. 1-2, pp. 83-86 (1989).
Glaum et al., "Identification of 5-HT₃ Binding Sites in Rat Spinal Cord Synaptosomal Membranes", Europ. J. of Pharmacol., vol. 156, pp. 287-290 (1988).

(Continued)

*Primary Examiner*—Brian-Yong S Kwon
(74) *Attorney, Agent, or Firm*—Wenderoth, Lind & Ponack, L.L.P.

(57) ABSTRACT

The present invention relates to a new use for compounds having 5-HT₃ (serotonin M) receptor antagonist activity, especially tropisetron, for the manufacture of a pharmaceutical composition for the treatment of a non-inflammatory local disease of the musculo-sceletal system, of a local irritation condition of a joint or tendon sheath, or for the local treatment a local manifestation at the locomotor apparatus of an inflammatory disease except for a crystal induced arthritis and a living pathogen induced inflammatory disease condition as long as the living pathogen is still present.

8 Claims, No Drawings

OTHER PUBLICATIONS

Glaum et al., "Reversal of the Antinociceptive Effects of Intrathecally Administered Serotonin in the Rat by a Selective 5-$HT_3$ Receptor Antagonist", Neuroscience Letters, vol. 95, pp. 313-317 (1988).

Giordano et al., "Differential Analgesic Actions of Serotonin 5-$HT_3$ Receptor Antagonists in the Mouse", Neuropharmacology, vol. 28, No. 4, pp. 423-428 (1989).

Grubb et al., "A Study of 5-HT-Receptors Associated With Afferent Nerves Located in Normal and Inflamed Rat Ankle Joints", Agents and Actions, vol. 25, Nos. 3 and 4, pp. 216-218 (1988).

Stratz et al., "Topical Treatment of Inflammatory Joint Affections With the 5-HT3 Receptor Antagonist Tropisetron", Letter to the Editor (1999).

Chemical Abstracts XP-002149133 Fujii et al., "Prophylactic Antiemetic Therapy With Granisetron-Dexamethasone Combination in Women Undergoingg Breast Surgery", Acta. Anaesthesiologica Scandinavica, vol. 42, No. 9, pp. 1038-1042 (1998)—[PREV199800515648].

Chemical Abstracts XP-002149135 Pramanik et al., "Serotonin-3 (5$HT_3$) Receptor Antagonists Modulate Antinociceptive Responses in Mice", Indian Journal of Physiology and Allied Sciences, vol. 50, No. 4, pp. 168-172 (1996)—[PREV199799649054].

Chemical Abstracts XP-002149136 Samborski et al., "The 5-$HT_3$ Blockers in the Treatment of the Primary Fibromyalgia Syndrome: A 10-Day Open Study With Tropisetron At a Low Dose", Materia Medica Polona, vol. 28, No. 1, pp. 17-19 (1996)—[PREV199799477436].

Chemical Abstracts XP-002149137 Fujii et al., "Granisetron and Dexamethasone Provide More Improved Prevention of Postoperative Emesis Than Granisetron Alone in Children", Canadian Journal of Anaesthesia, vol. 43, No. 12, pp. 1229-1232 (1996)—[PREV199799339428].

Chemical Abstracts XP-002149138 Moser, "The Effect of 5-$HT_3$ Receptor Antagonists on the Writhing Response in Mice", General Pharmacology, vol. 26, No. 6, pp. 1301-1306 (1995)—[PREV199598457877].

Chemical Abstracts XP-002149142 Eschalier et al., "Influence of a Specific 5-HT3 Antagonist on Carrgeenan-Induced Hyperalgesia in Rats", vol. 36, No. 2 (1989)—[PREV198987128603].

Doak et al., "Formalin-Induced Nociceptive Behavior and Edema: Involvement of Multiple Peripheral 5-Hydroxytryptamine Receptor Subtypes", Neuroscience, vol. 80, No. 3, pp. 939-949 (1997).

Cunningham et al., "Optimum Anti-Emetic Therapy For Cisplatin Induced Emesis Over Repeat Courses: Ondansetron Plus Dexamethasone Compared With Metoclopramide, Dexamethasone Plus Lorazepam", Annals of Oncology, vol. 7, No. 3, pp. 277-282 (1996).

Chemical Abstracts XP-002149157 Botella et al., "Intracolonic Glycerol Induces Abdominal Contractions in Rats: Role of 5-HT3 Receptors", Fundamental & Clinical Pharmacology, vol. 12, No. 6, pp. 619-623 (1998)—[PREV 199900012906].

Chemical Abstracts XP-002149158 Samborski et al., "New Concept of Pharmacological Treatment of Fibromyalgia. Do Exist Two Subgroups of Fibromyalgia Patients?", Reumatologia, vol. 36, No. 2, pp. 144-150 (1998)—[PREV199800453416].

Rosenstein, Abstract XP-000886228, Antinociceptive Effects of Microdialysis Administration of 5-HT1A and 5 HTReceptor Aagonists and Antagonists in a Model of Acute Arthritis. Society for Neurosciende Abstracts, US, Society for Neuroscience, vol. 23, No. p. 1540.

* cited by examiner

USE OF 5-HT₃ RECEPTOR ANTAGONISTS FOR TREATING MUSCULOSKELETAL DISEASES

This is a divisional application of U.S. application Ser. No. 09/929,454, now U.S. Pat. No. 6,462,065, which is a continuation of Application No. PCT/EP00/01269 filed Feb. 16, 2000.

The present invention relates to a new use, in particular a new pharmaceutical use for compounds having $5\text{-}HT_3$ (serotonin M) receptor, in particular specific $5\text{-}HT_3$ receptor, antagonist activity, especially in the manufacture of a pharmaceutical composition.

Specifically, the present invention relates to the treatments defined below.

The $5\text{-}HT_3$-receptor antagonists comprise a defined and recognised class of pharmaceutically active compounds well known in the art and characterised, as their name implies, by their pharmacological activity. Various $5\text{-}HT_3$ receptor antagonist compounds are commercially available and clinically applied, e.g. in the treatment of emesis.

In accordance with the present invention it has now surprisingly been found that $5\text{-}HT_3$ receptor antagonists are useful for the treatment of local non-inflammatory, local irritation-related and local inflammatory disease conditions. This is surprising in that (a) the $5\text{-}HT_3$ receptor antagonists are effective alone; (b) do not only bring pain relief, but also are effective in the treatment of other symptoms, such as effusion, swelling, stiffness and the like, and (c) are locally effective, thus not having to rely on systemic administration that may show effects e.g. by working via effects on nerves and/or synapses at the spinal cord. It is also astonishing that relatively high local doses are both tolerated and effective when local administration is employed.

Hence, the present invention relates to the use of a $5\text{-}HT_3$ receptor antagonist or of a pharmaceutically acceptable salt of such an antagonist for the manufacture of a pharmaceutical composition for the treatment of a non-inflammatory local disease of the musculo-sceletal system, of a local irritation condition of a joint or tendon sheath, or for the local treatment a local manifestation at the locomotor apparatus of an inflammatory disease except for a crystal induced arthritis and a living pathogen induced inflammatory disease condition as long as the living pathogen is still present for example the treatment of any process, condition, event, or disease as hereinafter described. In particular, the present invention provides the use as mentioned before where, in addition to pain at least one further sequela or symptom of the local disease, local irritation condition or local manifestation is alleviated, ameliorated or controlled.

Any $5\text{-}HT_3$ receptor antagonist can be used in accordance with the invention. Preferred $5\text{-}HT_3$ receptor antagonists which may be employed in accordance with the present invention are:

A) Ondansetron [1,2,3,9-tetrahydro-9-methyl-3-[(2-methyl-IH-imidazol-1-yl]methyl]-4H-carbazol-4-one (cf. Merck Index, twelfth edition, item 6979);

B) Granisetron [endo-1-methyl-N-(9-methyl-9-aza-bicyclo [3.3.1]non-3-yl)-IH-imidazole-3-carboxamide: (cf. loc. cit., item 4557); and C) Dolasetron [IH-indole-3-carboxylic acid (2α, 6α, 8α, 9αβ)-octahydro-3-oxo -2,6-methano-2H-quinolizin-8-yl ester] (cf. loc. cit., item 3471).

Particular $5\text{-}HT_3$ receptor antagonists which may be employed in accordance with the present invention are those of the formula 1 as defined in European Patent Publication 189002 B1, the contents of which are incorporated herein by reference, in particular the compound:

D) Indol-3-yl-carboxylic acid-endo-8-methyl-8-aza-bicyclo [3,2,1]-oct-3-yl-ester, also known as tropisetron. (cf. loc. cit., item 9914).

Further $5\text{-}HT_3$ receptor antagonists which may be used preferably in accordance with the present invention are:

E) 4,5,6,7-tetrahydro-5-[(1-methyl-indol-3-yl)carbonyl]benzimidazole (see also ramosetron, see U.S. Pat. No. 5,344, 927);

F) (+)-10-methyl-7-(5-methyl-1H-imidazol-4-ylmethyl)-6, 7,8,9-tetrahydropyrido[1,2-a]indol-6-one (see also fabesetron, EP 0 361 317); and G) [N-(1-ethyl-2-imidazolin-2-y-methyl)-2-methoxy-4-amino-5-chlorobenzamide (see also lintopride-Chem.-Abstr.-No. 107429-63-0).

A further $5\text{-}HT_3$ receptor antagonists which may be used preferably in accordance with the present invention is H) 2,3,4,5-tetrahydro-5-methyl-2-[(5-methyl-1H-imidazol-4-yl)methyl]-1H-pyrido[4,3-b]indol-1-one (see also alosetron, EP 0 306 323).

$5\text{-}HT_3$-receptor antagonists may be employed in accordance with the invention in free or in pharmaceutically acceptable salt form, e.g. as known in the art, for example, in the case of compounds A) to D) above in pharmaceutically acceptable acid addition salt form, for example, in the case of: compound A) the hydrochloride dihydrate; compound B) the hydrochloride; compound C) the mesylate; and compound D) the monohydrochloride. References to $5\text{-}HT_3$ receptor antagonists collectively or individually throughout the present specification and claims are accordingly to be understood as embracing both free compounds and such pharmaceutically acceptable salt forms, e.g. as clinically employed, and further also solvates, e.g. hydrates, or specific crystal forms of any of these compounds or salts.

For use in accordance with the present invention tropisetron (especially in the formulation called NAVOBAN®) is most preferred.

Thus, the invention relates to the use of a $5\text{-}HT_3$ receptor antagonist or of a pharmaceutically acceptable salt of such an antagonist for the manufacture of a pharmaceutical composition for the treatment of a non-inflammatory local disease of the musculo-sceletal system, of a local irritation condition of a joint or tendon sheath, or for the local treatment a local manifestation at the locomotor apparatus of an inflammatory disease except for a crystal induced arthritis and a living pathogen induced inflammatory disease condition as long as the living pathogen is still present, where the $5\text{-}HT_3$ receptor antagonist is selected from the group consisting of ondansetron, granisetron, dolasetron, tropisetron, ramosetron, fabesetron, lintopride and alosetron, which may be used in free form or as a pharmaceutically acceptable salt.

In accordance with the present invention it has now surprisingly been found that $5\text{-}HT_3$ receptor antagonists are useful for the treatment of certain diseases, processes, conditions or events, namely non-inflammatory local diseases of the musculo-sceletal system; local irritation conditions of the joints or tendon sheaths; or the local treatment also of local manifestations at the locomotor apparatus of inflammatory diseases; such as conditions, processes or events that are due to trauma (including surgery or preferably accident); overload; posture fault; degenerative processes; conditions subsequent to another disease (including infection, for example viral infection, or tumor diseases); or other conditions that result in irritation of the locomotor apparatus of the body; meaning especially therapy of the respective non-inflammatory disease, irritation or manifestation as such, its sequelae or its symptoms, or any combinations of these.

"Treatment" as used herein includes use for the alleviation, amelioration or control of said diseases, processes, conditions or events. It also includes intervention for the alleviation, amelioration or control of the sequelae or symptoms of any one or more of these diseases, for example degeneration (e.g. of cells, epithelia or tissues), swelling, exudation, effusion or pain, stiffness or inflexibility of joints. In this context the term "treatment" is further to be understood as embracing use to reverse, restrict or control progression of any specified disease, process, condition event or the like, including use for disease modifying effect. If any of the mentioned diseases, processes, conditions, manifestations or events, especially an inflammatory disease, process, condition, manifestation or event, is associated with pain, the term "treatment" preferably encompasses the alleviation, amelioration or control (including temporal or permanent removal) of at least one further sequela or symptom in addition to pain, such as swelling, effusion, exsudation, lack of flexibility (e.g. due to stiffness and/or lack of flexibility of joints), loss of strength or degeneration, more preferably of all symptoms and most preferably of the total clinical picture of the respective disease, irritation or manifestation. According to the present invention, the term "treatment" preferably does not have the meaning of prevention.

The present invention is in particular applicable to the treatment of:

(1) non-inflammatory local diseases of the musculo-sceletal system (including a joint or another part of the locomotor apparatus), such as
  (1a) myofasciale syndrome, including myelogelosis, chronic lumbalgia or cervicalgia, for example unspecific or in the context of degenerative spinal affections, of static posture fault or malformation of the spine, e.g. cervical syndrome,
  (1b) tendomyosis, tendinosis, insertion tendopathy (e.g. epicondylitis), bursopathy or periarthropathy,
  (1c) overload syndrome of the muscle,
  (1d) syndromes due to the compression of nerves or neuropathy (such as medianus compression syndrome=carpal tunnel syndrome), or
  (1e) algodystrophy (also called neurodystrophy); or
(2) local irritation conditions (=states of irritation) of a joint or tendon sheath especially related to
  (2a) a meniscus lesion (e.g. following surgical intervention or preferably due to damage to the meniscus due to a different cause),
  (2b) arthrosis, such as gonarthrosis,
  (2c) trauma, including accident or post-operative trauma, e.g. after implant or insertion surgery or endoscopy,
  (2d) osteochondritis dissecans, osteonecrosis or joint chondromatosis,
  (2e) or various non-inflammatory rheumatoid diseases, preferably to the local treatment of one or more of the mentioned diseases under (1) and/or (2); or
(3) to the local treatment also of a local manifestation at the locomotor apparatus of an inflammatory disease, such as various inflammatory rheumatoid diseases (except for crystal induced arthritis (e.g. gout) and except for living pathogen induced diseases as long as the living pathogen (bacterium, virus or fungus, protozoon, parasite or the like) is still present), such as
  (3a) chronic polyarthritis (=rheumatoid arthritis), including juvenile arthritis or psoriasis arthropathy;
  (3b) sarcoidosis,
  (3c) paraneoplastic syndrome or tumor-induced inflammatory diseases,
  (3d) turbid effusions,
  (3e) collagenosis, such as systemic Lupus erythematosus, poly-myositis, dermato-myositis, systemic sclerodermia or mixed collagenosis;
  (3f) postinfectious arthritis (where no living pathogenic organism can be found at or in the affected part of the body), or
  (3g) seronegative spondylarthritis, such as spondylitis ankylosans; or further
  (3h) vasculitis.

In the case of the inflammatory diseases, diseases where a living pathogen, e.g. a virus, a bacterium, a fungus, a protozoon or a parasite or the like, is still present, the treatment of must first aim at removal of the pathogen causative for the disease, before treatment with a 5-$HT_3$ antagonist is used, as otherwise there is the danger that the causative pathogen remains intact. Then the mere symptomatic treatment with a 5-$HT_3$ antagonist is contraindicated in order to avoid survival or even further spread of the causative infection. This is also valid in the case of combination with an anti-inflammatory glucocorticosteroid as described in the following, as is the proviso that treatment of crystal-induced inflammation is excluded.

The term "locomotor apparatus" refers to any component of the musculo-sceletal system of the body, especially to bony tissue, muscle, tendons, ligaments, joints, cartilage, perichondrium, periosteum, synovial membrane, bursa and the like.

"Trauma" refers preferably to operative and more preferably to trauma by accident, such as overload, tumble or push.

The term "local treatment" refers to the treatment with one or more 5-$HT_3$ receptor antagonists near or at the site of the manifestation of the disease to be treated, e.g. by intra-muscular injection, intra-articular injection, or any other injection near or at the site of disease manifestation (that is, preferably the administration has the goal to provide for locally higher concentrations of the administered compound than would be expected to be achieved by systemic administration, or the goal is not systemic exposure), preferably within an area within 20, more preferably 10 cm, still more preferably within 5 cm, around the outer limitation of the manifestation of the local disease, most preferably directly at the affected are or site, e.g. the are or site of symptom manifestation, such as the area of greatest pain, such as an insertion point, a trigger point or a joint, or also in a broader aspect of the invention by local tissue infiltration or transdermal administration at the site of the manifestation of the disease, e.g. by means of topical administration e.g. by use of gels, creams or ointments or the like, or by transdermal patch technology. In the case of the non-inflammatory diseases mentioned above under (1) and (2), also systemic treatment is possible, e.g. by enteral, especially peroral, e.g. by use of tables or capsules, or rectal, e.g. by use of enemation or suppositories; subcutaneous, intraperitoneal or intra-muscular injection; or infusion is possible. In the case of intravenous administration bolus injection is preferred. However, local treatment is preferred in all cases. An advantage of local treatment is that high efficiency can be reached and that systemic exposure to a 5-$HT_3$ antagonist can be diminished or avoided. One preferred local way of administration is the intra-articular injection in case of diseases, conditions etc. that relate to joints, e.g. bursopathy or synovitis.

A preferred example of a local manifestation at the locomotor apparatus of an inflammatory disease is synovial inflammation, for example, synovitis, including any of the particular forms of synovitis recited in Doriand's Illustrated Medical Dictionary, 26th edition, pub. W. B. Saunders and Co. at page 1301, as far as it is not crystal-induced. Such synovial inflammation may for example, be consequential to or associated with disease, e.g. arthrosis, including arthritis, e.g. osteoarthritis, rheumatoid arthritis or arthritis deformans.

Further preferred local diseases to be treated according to the invention are those mentioned in the examples.

From the foregoing it will be noticed that the present invention is to be understood especially as embracing the treatment, e.g. therapy, of any disease, process, symptom, event or condition as set forth above, for example for the alleviation or control of non-inflammatory local diseases or irritations or local inflammatory processes or events and the sequelae associated therewith or consequential thereto, e.g. to alleviate or control joint irritation or effusion; with the proviso that if pain is treated, then in addition at least one other disease manifestation (e.g. effusion, swelling, exudation or degeneration) is treated.

Preferably the present invention relates to the treatment, especially the local treatment, of a disease as mentioned above under (2) or (3), more preferably one of the diseases mentioned there other than algodystrophy and vasculitis.

In a further aspect it has been found in accordance with the present invention that 5-HT$_3$ receptor antagonists are useful as replacement therapy for local glucocorticosteroid, e.g. cortisone or the like, therapy; for example for use in any means of treatment as hereinbefore and hereinafter set forth, e.g. the diseases mentioned under (2) and (3) hereinabove.

The term "replacement therapy" as used herein is to be understood as embracing both use "as full replacement", i.e. use instead of glucocorticosteroid therapy, as well as use "as partial replacement" for glucocorticosteroid therapy, i.e. for administration together with glucocorticosteroid therapy or as a means of reducing glucocorticosteroid dosage or to achieve a glucocorticosteroid sparing effect.

The present invention accordingly provides:

I. A method of treating any process, condition, event, or disease as hereinbefore set forth, in a subject in need thereof, which method comprises locally administering an effective amount of a 5-HT$_3$ receptor antagonist, especially locally at or near the site of the local disease, local irritation condition or local manifestation;

II. A method of providing replacement therapy for glucocorticosteroid therapy in a subject receiving such glucocorticosteroid therapy for or in the treatment of any process, condition, event or disease as hereinbefore set forth, which process comprises locally administering to said subject an effective amount, e.g. a glucocorticosteroid sparing amount, of a 5-HT$_3$-receptor antagonist; as well as III. A method of treating any process, condition, event or disease as hereinbefore set forth, in a subject in need thereof, which method comprises locally administering an effective amount of a 5-HT$_3$ receptor antagonist together with a glucocorticosteroid.

Where the term "glucosteroid" is used, this means an anti-inflammatory glucosteroid.

Where co-administration is practiced as under III above the drug substances, i.e. 5-HT$_3$ receptor antagonist and glucocorticosteroid may be administered sequentially or simultaneously or substantially simultaneously, e.g. employing a fixed combination dosage form.

In further aspects the present invention also provides:

IV. A 5-HT$_3$ receptor antagonist for use in, or for use in the manufacture of a pharmaceutical composition for use in; or the use of a pharmaceutical composition comprising a 5-HT$_3$ receptor antagonist for local use:

a) in the treatment of any process, condition, event or disease as hereinbefore set forth;

b) as replacement therapy for glucocorticosteroid therapy in the treatment of any process, condition, event or disease as hereinbefore set forth; or c) for co-administration together with a glucocorticosteroid in the treatment of any process, condition, event or disease as hereinbefore set forth; and/or:

V. A pharmaceutical dosage form comprising a 5-HT$_3$ receptor antagonist together with a glucocorticosteroid, especially for the local treatment of any process, condition, event or disease as hereinbefore set forth.

Where under (I) to (V) the term "any process, condition, event or disease" is used, this term preferably relates to the diseases mentioned under (1), (2) and (3) above, especially as defined above as being preferred.

The term "locally administering" or "local use" is defined to mean local administration or especially "local treatment" as defined above, that is, administration at or near the site of the non-inflammatory disease, irritation condition or local inflammatory disease condition, in contrast to systemic administration.

Dosage forms, e.g. in accordance with V above, are to be understood as including both fixed-unit-dosage forms, e.g. liquid formulations, comprising both active ingredients together with appropriate pharmaceutically acceptable diluents or carriers, as well as twin delivery systems, packages or the like comprising both active ingredients separately or in separate dosage form, for concommitant or sequential administration.

The 5-HT$_3$ receptor antagonists are preferably used in well-known liquid formulations.

Utility of 5-HT$_3$ receptor antagonists in accordance with the present invention can be demonstrated in clinical trials carried out in accordance with standard techniques and methodologies, for example as follows:

The following examples are for illustrative purposes and are not intended to diminish the scope of the present invention. Instead of tropisetron, any other 5-HT$_3$-antagonist, or a pharmaceutically acceptable salt thereof, solvate, e.g. hydrate, or crystalline form thereof, especially selected from the group consisting of ondansetron, granisetron, dolasetron, ramosetron, fabesetron, lintopride and alosetron, can be used, or any combination of two or more of these 5-HT$_3$ receptor antagonists or pharmaceutically acceptable salts thereof.

In the following examples, tropisetron is administered in the standard formulation of the trademark Navoban® which is available in ampoules that contain 2 mg or 5 mg of the active substance, tropisetron.

EXAMPLE 1

Treatment of Synovial Inflammation/synovitis Consequent to Inflammatory Processes Trials are performed on 2 patients exhibiting rheumatoid arthritis and severe consequential synovial inflammation as well as marked pain.

Two patients exhibiting acute exacerbation of rheumatoid arthritis, one in the shoulder joint, the other in the knee joint, are each treated once with 2 mg tropisetron administered intraarticularly. In both cases treatment leads to almost complete remission from pain within a few hours. Both patients are examined over a period of one week following treatment with tropisetron and are found to be free of symptoms.

EXAMPLE 2

Treatment of Synovial Inflammation Following Traumatic or Degenerative Event A first patient exhibits repeated exudation from the knee joint consequential to damage to the meniscus. Prior to the trial the patient received injections of glucocorticoid. The patient receives an injection of 2 mg of tropisetron administered intra-articularly. After 45 min. marked reduction of pain is reported and a major reduction of effusion from the knee joint is observed after 5 hours. The patient remains free of symptoms without further therapy over an observation period of 5 days.

A second patient exhibits damage to the meniscus of the right knee joint as well as arthritic change leading to synovial irritation with consequential knee joint effusion. Despite a successful synovialectomy prior to trial entry the patient exhibits renewed knee joint effusion. Two 2 mg doses of tropisetron are administered i.v. over a period of 17 days with 15 injections, one each day with a 2 days pause in therapy. 24 hours after the first i.v. injection, significant improvement of pain is reported. Following continuation of injections, the patient exhibits as virtually free of symptoms. The exudation from the knee joint is completely inhibited without any other medication within 8 days and movement of the knee joint is clearly improved. The improvement in condition continues over a further 7 days observation following completion of therapy:

EXAMPLE 3

Treatment of Implant or Insertion Tendopathy

Three patients exhibiting implant/insertion tendopathy are treated with tropisetron. The condition treated results in the case of the first patient from epicondylitis radialis, in the case of the second patient from insertion tendopathy in the area of insertion of the deltoid muscle and, in the case of the third patient from an enthesiopathy of the Malleolus lateralis. In all three cases, tropisetron is injected once at a dosage of 2 mg in the area of greatest pain, directly into the tissues. In all three cases severity of pain decreases within a period of 60 min. and virtually complete remittal is achieved within 24 hrs., indicating remission from disease remission. Further improvements found after tropisetron injection include increase of strength and of flexibility of the affected body part.

EXAMPLE 4

Further Examples for the Efficiency of Tropisetron

Pain is subsequently determined on a visual analogue scale (VAS) that goes from 0 mm (no pain) to 100 mm (strongest pain).
4a) Enthesiopathy (Insertion Tendopathy) (with infiltration):
(i) Female patient, born in 1955; Diagnosis: epicondylitis. Rest pain before local injection of tropisetron 30 mm, 7 days later 0 mm.
(ii) Female patient, born 1947, diagnosis: periarthropathia humeroscapularis. Rest pain before local injection of tropisetron 85 mm, 7 days after local injection 45 mm.
(iii) Patient born 1953, diagnosis: epicondylitis. Rest pain before local injection of tropisetron 35 mm, 7 days thereafter 0 mm.
4b) Rheumatoid arthritis (intraarticular injection):
(i) Female patient, born 1942.
Before injection of Navoban into the right knee joint: rest pain 62 mm, pain under exercise 82 mm, bending up to 105°, knee joint circumference 46 cm. 24 hours later: rest pain 22 mm, pain under exercise 21 mm, bending 105°, knee joint circumference 45 cm. 48 hours after treatment: rest pain 0, pain under exercise 5 mm, bending 110°, knee joint circumference 45 cm. 7 days after treatment: rest pain 20 mm, pain under exercise 16 mm, bending up to 145°, knee joint circumference 45.4 cm.
(ii) Female patient, born 1947.
Before injection of 2 mg Navoban into the left knee joint: rest pain 25 mm, pain under exercise 85 mm, bending up to 115°, knee joint circumference 37.5 cm. 24 hours later: rest pain 8 mm, pain under exercise 58 mm, bending 120°, knee joint circumference 37.5 cm. 48 hours after treatment: rest pain 6 mm, pain under exercise 55 mm, bending 115°, knee joint circumference 37.5 cm. 7 days after treatment: rest pain 5 mm, pain under exercise 59 mm, bending up to 115°, knee joint circumference 37 cm. Now 5 mg Navoban are injected into the knee joint, 7 days later the patient has a rest pain of 0 mm, pain under exercise of 33 mm, bending is possible up to 120°, and the knee joint circumference is 37.5 mm.
4c) Treatment of left knee joint irritation (Morbus Still):
Patient, 26 year old, Morbus Still diagnosed 1.5 years ago. Despite basic treatment with 15 mg methotrexat per week and 20 mg prednisolone per day, the patient suffers from swelling and overheating of the left knee joint for the first time in February 1999. Pain at rest in the VAS 98 (0-100), pain under strain 70. Obvious articular effusion. Knee joint circumference 44 cm, straightening/bending 0°-10°, 115°. 24 hours after an intraarticular injection with 2 mg tropisetron pain at rest in the Visual Analog Scale (VAS) 0, pain under strain 70. Straightening/bending 0°, 0°,135°, knee joint circumference 41 cm, with significant reduction of joint swelling and effusion respectively. 7 days later pain at rest in the VAS 0, pain under strain 57, straightening/bending 0°,0°,130°, knee joint circumference 40.5 cm.
4e) Gonarthrosis:
Patient, 74 years old, has activated gonarthritis with effusion for 2 months. Only short-term pain reduction by means of non-steroidal antiphlogistics could be achieved. Following an intra-articular injection with 2 mg tropisetron, pain at rest after 24 hours on the visual analog scale for pain (0-100) sinks from 43 to 25, after 2 days to 13, after 7 days to 10 and in a follow-up check after 17 days to 4. The analog values for pain under strain are 75, 45, 10 and 10, respectively. The effusion is gone after 7 days, as is the overheating of the knee joint.

EXAMPLE 5

Spinal Syndrome (i.v. Administration)

Female patient born 1957, diagnosis: cervical syndrome. Before injection of 2 mg tropisetron 68 mm rest pain, 24 hours later 35 mm, at day 7 18 mm.

EXAMPLE 6

Spinal Syndromes (i.v. Administration)

(i) Cervical Syndrome:
Female patient born 1957, diagnosis: cervical syndrome. Before i.v. injection of 2 mg tropisetron 68 mm rest pain, 24 hours later 35 mm, at day 7 18 mm.
(ii) Lumbalgia:
Patient born 1940, diagnosis: lumbalgia. The patient is injected 2 mg Navoban i.v., the rest pain before the injection amounts to 78 mm, the pain under exercise 90 mm, the Schober distance upright/with bended upper part of the body between the processus spinalis vertebrae of vertebra 1 and 5 ("Schober" hereinafter) 10/11 cm, the distance from fingers to ground with bended upper part of the body 32 cm; 24 hours later, the rest pain is 36 mm, the pain under exercise 43 mm, the Schober 10/12.3, and the finger/ground distance 24 cm; after 48 hours, the rest pain is 28 mm, the pain under exercise 47 mm, the Schober 10/12.5, the finger/ground distance 26.5 cm. 7 days after treatment, the rest pain is 15 mm, the pain under exercise 22 mm, the Schober 10/13, and the finger/ground distance 22 cm.

Equivalent results as in the preceding examples are obtainable in equivalent or comparable trials with patients exhibiting similar symptomatology employing 5-$HT_3$-receptor antagonists other than tropisetron, for example using any of the 5-$HT_3$-receptor antagonists A) through C) or E) through H) hereinbefore recited at comparable, e.g. conventional clinical, dose as known in the art. Similar results are also achievable employing 5-$HT_3$ receptor antagonists, e.g. tropisetron at doses of the order of 2 mg/day p.o. or by injection or topical application in clinical trials involving subjects exhibiting other local non-inflammatory or local inflammatory diseases, conditions or symptoms.

Trials conducted as described above or analogously are demonstrative of long lasting and disease modifying effects in conditions herein described as well as symptomatic and glucocorticosteroid replacement effect for 5-$HT_3$ receptor antagonists.

For use in accordance with the present invention the appropriate dosage will, of course, vary depending on for example the particular 5-$HT_3$ receptor antagonist employed the mode of administration and the nature and severity of the condition to be treated as well as the specific condition to be treated. In general an indicated single, e.g. daily, dosage will be in the range usually employed for known indications such as emesis and will typically be from about 0.05 to about 50 mg per day, more preferably around 1 to 10 mg per day, conveniently administered once or in divided doses up to four times a day or in sustained release form, or used repeatedly after longer intervals, e.g. after some days or weeks, e.g. after 2 days to 4 weeks. In the case of tropisetron an appropriate dosage for administration, e.g. by injection, for example for i.v. application or injection direct into the affected areas, will be of the order of 2 mg per day or 5 mg per day, administered once, sequentially over a sequence of 2 to 20 days or at intervals of 2 to 5 days to 2 days to 2 weeks.

For use in accordance with the invention, 5-$HT_3$ receptor antagonists may be administered by any conventional route in particular enterally, preferably orally, e.g. in the form of tablets or capsules, or rectally, e.g. in the form of suppositories or enemation, or most preferably parenterally, e.g. in the form of injectible solutions or suspensions, e.g. by subcutaneous, intraperitoneal or intramuscular injection for systemic administration. Suitable formulations for use in accordance with the present invention will include any of those as known and commercially available and clinically employed in the art, for example the commerically available formulations. Preferably, the compositions are administered locally, that is, near or at the site of the manifestation of the disease to be treated, e.g. by intramuscular injection, intra-articular injection or any other injection near or at the site of disease manifestation; in a broader aspect of the invention, also local tissue infiltration or transdermal administration may be considered, e.g. by use of gels, creams or ointments or the like, or preferably by transdermal patches. Dosages for such forms will be of the order or slightly higher than those used on administration by injection.

The invention claimed is:

1. A method of treating a) a non-inflammatory local disease of the musculo-skeletal system which is myofascial syndrome, tendomyosis, tendinosis, insertion tendopathy, bursopathy, periarthropathy, or algodystrophy; b) a local irritation condition of a joint or tendon sheath caused by a meniscus lesion, arthrosis, trauma, local osteochondritis dissecans, osteonecrosis or joint chondromatosis; or c) a local manifestation at the locomotor apparatus of an inflammatory disease, wherein said inflammatory disease is selected from the group consisting of chronic polyarthritis, sarcoidosis, paraneoplastic syndrome, turbid effusions, collagenosis, postinfectious arthritis, seronegative spondylarthritis and vasculitis, in a subject in need thereof, which method comprises locally administering to said subject a pharmaceutical composition consisting essentially of an effective amount of a 5-$HT_3$ receptor antagonist.

2. The method of claim 1, wherein the disease to be treated is a local irritation condition of a joint or tendon sheath caused by a meniscus lesion, arthrosis, trauma, local osteochondritis dissecans, osteonecrosis or joint chondromatosis.

3. The method of claim 1 for local treatment of a local manifestation at the locomotor apparatus of an inflammatory disease, wherein said inflammatory disease is selected from the group consisting of chronic polyarthritis, sarcoidosis, paraneoplastic syndrome turbid effusions, collagenosis, postinfectious arthritis, seronegative spondylarthritis and vasculitis.

4. The method of claim 1, wherein the 5-$HT_3$ receptor antagonist is administered locally at or near the site of the local disease, local irritation condition or local manifestation.

5. The method according of claim 1 wherein the 5-$HT_3$ receptor antagonist is tropisetron.

6. The method of claim 1 wherein the 5-$HT_3$ receptor antagonist is selected from the group consisting of ondansetron, granisetron, dolasetron, tropisetron, ramosetron, fabesetron, lintopride and alosetron or pharmaceutically acceptable salts thereof.

7. The method of claim 4 wherein the 5-$HT_3$ receptor antagonist is selected from the group consisting of ondansetron, granisetron, dolasetron, tropisetron, ramosetron, fabesetron, lintopride and alosetron or pharmaceutically acceptable salts thereof.

8. The method of claim 4 wherein the 5-$HT_3$ receptor antagonist is tropisetron.

* * * * *